United States Patent
Boyd et al.

(10) Patent No.: US 9,289,369 B2
(45) Date of Patent: Mar. 22, 2016

(54) NON-AQUEOUS ORAL CARE COMPOSITION CONTAINING DENTAL OCCLUSION ACTIVES

(75) Inventors: Thomas James Boyd, Metuchen, NJ (US); Suman Kumar Chopra, Monroe, NJ (US); Sarita Vera Mello, North Brunswick, NJ (US); Rahul Patel, Parsippany, NJ (US); Dennis Kembero Ontumi, Easton, PA (US)

(73) Assignee: Colgate-Palmolive Company, New York, NY (US)

(*) Notice: Subject to any disclaimer, the term of this patent is extended or adjusted under 35 U.S.C. 154(b) by 107 days.

(21) Appl. No.: 13/995,440

(22) PCT Filed: Dec. 20, 2010

(86) PCT No.: PCT/US2010/061324
§ 371 (c)(1),
(2), (4) Date: Jun. 18, 2013

(87) PCT Pub. No.: WO2012/087281
PCT Pub. Date: Jun. 28, 2012

(65) Prior Publication Data
US 2013/0263395 A1    Oct. 10, 2013

(51) Int. Cl.
*A61K 8/81*    (2006.01)
*A61Q 11/00*    (2006.01)
*A61K 8/11*    (2006.01)
*A61K 8/24*    (2006.01)
*A61K 8/44*    (2006.01)
*A61K 8/65*    (2006.01)
*A61K 8/92*    (2006.01)

(52) U.S. Cl.
CPC ............ *A61K 8/8164* (2013.01); *A61K 8/11* (2013.01); *A61K 8/24* (2013.01); *A61K 8/44* (2013.01); *A61K 8/65* (2013.01); *A61K 8/922* (2013.01); *A61Q 11/00* (2013.01); *A61K 2800/31* (2013.01)

(58) Field of Classification Search
USPC ............................................. 424/52, 49, 53
See application file for complete search history.

(56) References Cited

U.S. PATENT DOCUMENTS

| | | | |
|---|---|---|---|
| 4,196,189 A * | 4/1980 | Raaf et al. ............... | 424/456 |
| 4,292,304 A | 9/1981 | Barels et al. | |
| 4,422,985 A | 12/1983 | Morishita et al. | |
| 4,426,337 A | 1/1984 | Suzuki et al. | |
| 4,521,551 A | 6/1985 | Chang et al. | |
| 4,808,401 A * | 2/1989 | Gaffar et al. .............. | 424/52 |
| 5,028,432 A | 7/1991 | Chopra et al. | |
| 5,300,305 A | 4/1994 | Stapler et al. | |
| 5,390,984 A | 2/1995 | Boucherie et al. | |
| 5,393,796 A | 2/1995 | Halberstadt et al. | |
| 5,478,570 A | 12/1995 | Sunohara et al. | |
| 5,533,791 A | 7/1996 | Boucherie | |
| 5,543,443 A | 8/1996 | Rajaiah et al. | |
| 5,561,177 A | 10/1996 | Khaledi et al. | |
| 5,571,502 A | 11/1996 | Winston et al. | |
| 5,609,890 A | 3/1997 | Boucherie | |
| 5,961,958 A * | 10/1999 | Homola et al. ............ | 424/49 |
| 6,306,435 B1 | 10/2001 | Chen et al. | |
| 6,524,558 B2 | 2/2003 | Kleinberg et al. | |
| 6,696,045 B2 | 2/2004 | Yue et al. | |
| 7,087,219 B2 | 8/2006 | Burzynski et al. | |
| 2005/0214230 A1 | 9/2005 | Mehta et al. | |
| 2006/0045854 A1 * | 3/2006 | Zaidel et al. ............... | 424/53 |
| 2008/0267891 A1 * | 10/2008 | Zaidel et al. ............... | 424/50 |
| 2008/0286214 A1 | 11/2008 | Brown et al. | |
| 2009/0202450 A1 | 8/2009 | Prencipe et al. | |
| 2009/0202456 A1 | 8/2009 | Prencipe et al. | |
| 2009/0311200 A1 | 12/2009 | Lambert et al. | |
| 2009/0320226 A1 | 12/2009 | Robinson et al. | |
| 2010/0135932 A1 | 6/2010 | Deckner et al. | |

FOREIGN PATENT DOCUMENTS

| | | |
|---|---|---|
| JP | S57-182363 | 11/1982 |
| WO | WO 99/06031 | 2/1999 |
| WO | WO 2008/102321 | 8/2008 |
| WO | WO 2008/130764 | 10/2008 |
| WO | WO 2009/149030 | 12/2009 |
| WO | WO 2009/157956 | 12/2009 |
| WO | WO 2010/115041 | 10/2010 |
| WO | WO 2011/162756 | 12/2011 |

OTHER PUBLICATIONS

International Search Report and Written Opinion in International Application No. PCT/US10/061324, mailed Oct. 27, 2011.
Ofner et al., 1987, "Swelling Studies of Gelatin II: Effect of Additives," J. Pharm. Sci. 76(9):715-723.
Schiff et al., 1994, "Efficacy of a dentifrice containing potassium nitrate, soluble pyrophosphate, PVM/MA copolymer, and sodium fluoride on dentinal hypersensitivity: a twelve-week clinical study," J. Clin. Dentistry 5:87-92.
Thau et al., 1965, "A New Procedure for the Preparation of Polyethylene-Mineral Oil Gels," J. Soc. Cosmetic Chemists 16:359-363.
Written Opinion in International Application No. PCT/US10/061324, mailed Dec. 17, 2012.
Miller et al., 1994, "Evaluation of a New Dentifrice for the Treatment of Sensitive Teeth," The Journal of Clinical Dentistry V(Special Issue):71-79.
Pavlova, 2005, "Microstructure and reactivity of binary copolymerization products of maleic anhydride with vinyl chloride and vinyl acetate in solutions," Abstract of the dissertation for candidate of chemical science, Barnaul, pp. 5-15.

* cited by examiner

Primary Examiner — Walter Webb

(57) ABSTRACT

A oral care composition includes: (a) a hydrophilic film-forming polymer; and (b) a hydrophobic carrier, wherein the hydrophilic film-forming polymer is a film-forming polymer effective to occlude dentinal tubules and the oral care composition contains 0-10 wt. % water. The hydrophilic film-forming polymer is preferably GANTREZ S. The hydrophobic carrier is preferably a vegetable oil. A method of cleaning teeth includes applying to the teeth the oral care composition such that the hydrophilic film-forming polymer occludes dentinal tubules. A toothbrush includes: a handle; a head mounted to the handle, the head comprising an outer surface and a plurality of tooth cleaning elements extending outwardly from the outer surface; and a gelatin capsule containing the oral care composition positioned on the head.

13 Claims, No Drawings

NON-AQUEOUS ORAL CARE COMPOSITION CONTAINING DENTAL OCCLUSION ACTIVES

FIELD OF THE INVENTION

The invention relates to oral care compositions for treating and/or prophylaxis of dentinal hypersensitivity, and oral care devices including same.

BACKGROUND

PCT/US2010/039677 discloses the use of arginine and a film-forming polymer of methylvinylether/maleic anhydride (GANTREZ S™) in a dual phase (aqueous/non-aqueous) mouthwash to form a highly adherent film, which is effective to occlude dentinal tubules, and thereby reduce tooth sensitivity.

Other publications disclosing the use of arginine and/or GANTREZ in oral care compositions include US 20090202456 A1, US 20090311200 A1 and US 20100135932 A1.

Schiff et al., "Efficacy of a oral care containing potassium nitrate, soluble pyrophosphate, PVM/MA copolymer, and sodium fluoride on dentinal hypersensitivity: a twelve-week clinical study." J Clin Dent. 1994; 5 Spec No:87-92, discloses that a oral care containing 5.0% potassium nitrate, 1.3% soluble pyrophosphate, 1.5% PVM/MA copolymer, and 0.243% sodium fluoride in a silica base provides significant improvement in dentinal hypersensitivity relative to a placebo lacking the potassium nitrate.

Non-aqueous oral care compositions are known in the art. See, e.g., U.S. Pat. No. 4,292,304, which discloses encapsulated oil based oral care compositions, which are substantially anhydrous; U.S. Pat. No. 5,571,502, which discloses a non-aqueous toothpaste or gel comprising water-soluble oral care actives in a hydrophilic, non-aqueous vehicle which is water soluble; U.S. Pat. No. 6,696,045, which discloses oral care compositions comprising water-unstable and/or co-reactive actives and less than about 10% water; and U.S. Pat. No. 7,087,219, which discloses a toothpaste consisting of oral care actives in a mineral oil carrier.

Despite the foregoing developments, it is desired to provide improved non-aqueous oral care compositions, which are effective to treat or prevent dentinal hypersensitivity.

BRIEF SUMMARY

Various embodiments described herein satisfy the aforementioned needs, by providing non-aqueous oral care compositions containing dental occlusion actives.

According to one aspect of the invention, a oral care composition comprises: (a) a hydrophilic film-forming polymer; and (b) a hydrophobic carrier, wherein the hydrophilic film-forming polymer is a film-forming polymer effective to occlude dentinal tubules and the oral care composition contains less than 10 wt. % water.

In certain embodiments, the oral care composition contains less than 1 wt. % water.

In certain embodiments, the hydrophilic film-forming polymer constitutes 2-5 wt. % of the oral care composition.

In certain embodiments, the hydrophilic film-forming polymer is an acid form of a copolymer of methyl vinyl ether and maleic anhydride.

In certain embodiments, the hydrophobic carrier comprises at least one member selected from the group consisting of an oil, a wax and silicone.

In certain embodiments, the hydrophobic carrier comprises at least one of a vegetable oil and silicone oil.

In certain embodiments, the hydrophobic carrier comprises a C6 to C12 triglyceride.

In certain embodiments, the hydrophobic carrier constitutes 55-85 wt. % of the oral care composition.

In certain embodiments, the oral care composition further comprises a polyphosphate, which is preferably at least one of Tetra Potassium Pyrophosphate (TKPP) and Tetra Sodium Pyrophosphate (TSPP). In such embodiments, the polyphosphate preferably constitutes 1-7 wt. % of the oral care composition.

In certain embodiments, the oral care composition is free of potassium salts and/or is free of guanidines.

In certain embodiments, the oral care composition has a flow reduction greater than 60% as measured with a flowmeter attached to a Pashley's cell.

In certain embodiments, the oral care composition further comprises 5-25 wt. % of a flavoring agent and 0.1-5 wt. % of a sweetening agent.

In certain embodiments, the oral care composition further comprises at least one member selected from the group consisting of an abrasive, an anti-bacterial agent, a foaming agent, a whitening agent, an anti-calculus agent, a tartar control agent, an anti-inflammatory agent, an anticaries agent, a flavoring agent, a sweetening agent and a colorant.

In certain embodiments, the oral care composition is encapsulated within a capsule comprising gelatin.

In certain embodiments, the oral care composition is a solid at 21° C.

According to another aspect of the invention, a method of cleaning teeth comprises applying to the teeth the oral care composition of the invention such that the hydrophilic film-forming polymer occludes dentinal tubules.

According to still another aspect of the invention, a toothbrush comprises: a handle; a head mounted to the handle, the head comprising an outer surface and a plurality of tooth cleaning elements extending outwardly from the outer surface; and a gelatin capsule containing the oral care composition of the invention positioned on the head.

DETAILED DESCRIPTION

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. In addition, the compositions and the methods may comprise, consist essentially of, or consist of the elements described therein.

Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% may include 9.5% or 10.5%, given the degree of error in measurement that will be appreciated and understood by those having ordinary skill in the art.

As used herein, terms "treatment" or "treating" are intended to include prophylaxis of a condition, as well as partial and/or complete amelioration of the condition. Persons of ordinary skill in the art of oral care compositions (to which the present method claims are directed) recognize that the term "prevent" is not an absolute term. Rather, the term is understood to refer to the prophylactic administration of a composition to diminish the likelihood or seriousness of a condition, and this is the sense intended.

An "orally acceptable amount" of a compound is an amount that is not harmful to a mammal when a composition containing such amount is retained in the mouth, without swallowing, for a period sufficient to permit application to an oral surface as provided herein. In general, such amount of the compound is not harmful even if the composition is unintentionally swallowed. An "orally acceptable carrier" denotes any vehicle or carrier that is not harmful to a mammal when such carrier is used in a composition that is retained in the mouth, without swallowing.

As discussed above, the compositions of the invention are preferably non-aqueous. As used herein, the expression "non-aqueous" means that the compositions do not include water in such an amount that it will prematurely trigger the activity of the active agent(s) in the composition, and/or reduce the stability of the composition. Preferably, the compositions of the invention include either no water or only traces of water from salts with water of hydration. Thus, in certain embodiments, no water is added to the composition prior to use.

Formulated oral care compositions such as tooth pastes and gels contain a number of functional and active ingredients, each of which contribute to at least one desirable property. Properly formulated oral care compositions are suitable for regular use to promote oral health. Functional additives include foaming agents that disperse other ingredients and provide for delivery of the active and functional materials to the oral surfaces, and tartar control agents to prevent the formation of calculus on tooth surfaces, as well as aesthetic functional ingredients such as flavors and pigments. Active ingredients include anticaries agents that provide a source of fluoride ion upon use. Various compositions also contain compounds or components with antibacterial properties, for example to reduce the formation of plaque on the surfaces. Further active ingredients include those with anti-inflammatory properties for prophylaxis and treatment of conditions such as gingivitis.

Throughout this description, the expression "oral care active" denotes a component that provides an active effect during an oral care treatment. Oral care actives include, but are not limited to foaming agents, antibacterial agents, whitening agents, anti-calculus agents, antimicrobial agents, tartar control agents, anti-inflammatory agents, anti-hypersensitivity agents and the like.

The invention was motivated in part by a desire to provide a non-aqueous oral care composition containing hydrophilic oral care actives effective to treat and/or prevent dentinal hypersensitivity. Although such hydrophilic oral care actives were known to be useful when dissolved in aqueous oral care compositions, it was unexpected that such hydrophilic oral care actives, which were conventionally believed to rely on mobility and solubility to impart their mode of action, could be effectively administered via a non-aqueous composition.

Thus, a basic embodiment of the inventive oral care composition comprises a hydrophilic film-forming polymer effective to treat dentinal hypersensitivity suspended in a hydrophobic carrier, wherein the composition is non-aqueous.

Suitable hydrophilic film-forming polymers may include additionally guanidines.

The film-forming polymer is preferably a synthetic 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000. The copolymers are generally employed in the form of their free acids or preferably partially or more preferably fully neutralized water soluble alkali metal (e.g., potassium and preferably sodium) or ammonium salts.

One particularly preferred film-forming polymer is a synthetic copolymer comprises poly(methylvinylether/maleic acid). In another embodiment, a copolymer comprises poly(methylvinylether/maleic acid) half esters. In another embodiment, a copolymer comprises poly(methylvinylether/maleic acid) mixed salts.

Polymers of any molecular weight may be used, including, for example molecular weights of 50,000 to 500,000, 500,000 to 2,500,000 or 2,500,000 to 10,000,000 (calculated by either number average or weight average). In a preferred embodiment, the copolymer has a molecular weight of 130,000. In an embodiment, a polymer has a molecular weight of 200,000. In an embodiment, a copolymer has a molecular weight of 690,000. In an embodiment, a copolymer has a molecular weight of 1,000,000. In an embodiment, a copolymer has a molecular weight of 1,250,000. In an embodiment, a copolymer has a molecular weight of 1,980,000. In another embodiment, a copolymer has a molecular weight of 2,500,000. In yet another embodiment, a copolymer has a molecular weight of 5,000,000.

Examples of these copolymers are available from ISP Corporation under the tradename GANTREZ, e.g., GANTREZ AN 139 (M.W. 1,100,000), GANTREZ AN 119 (M.W. 200,000); GANTREZ S-97 Pharmaceutical Grade (M.W. 1,500,000), GANTREZ AN 169 (M.W. 2,000,000), and GANTREZ AN 179 (M.W. 2,400,000); wherein the preferred copolymer is GANTREZ S-97 Pharmaceutical Grade (M.W. 1,500,000).

The film-forming polymer is provided in an amount effective to reduce dentinal hypersensitivity, and preferably constitutes 0.1-10 wt. % or 1-6 wt. % or 2-5 wt. % of the oral care composition.

A guanidine suitable for use with the hydrophilic film-forming polymer effective to treat dentinal hypersensitivity is a compound containing a guanidine group capable of forming a guanidinium ion under conditions present in the oral cavity. Suitable guanidine actives include but are not limited to arginine bicarbonate, arginine hydroxide, arginine carbonate, arginine phosphate, arginine organic phosphate, arginine phytate, aminoguanidine and aminoguanidinium analogues. L-arginine is particularly preferred.

The guanidine active is provided in an amount effective to reduce dentinal hypersensitivity, and when present, preferably constitutes 0.1-15 wt. % or 1-10 wt. % or 3-7 wt. % of the oral care composition. Certain embodiments of the invention are free of guanidines.

The hydrophilic film-forming polymer is preferably provided in the compositions of the invention in a safe and effective amount. Preferably, the hydrophilic film-forming polymer constitutes from 0.01 or 0.1 or 1 or 2 wt. % to 5 or 6 or 10 or 20 wt. % of the oral care composition. In certain embodiments, the hydrophilic film-forming polymer constitutes 0.1-20 wt. % or 1-10 wt. % or 2-5 wt. % of the oral care composition.

In addition to the hydrophilic film-forming polymer, oral care compositions of the invention further comprise a hydrophobic carrier, such as vegetable oil and/or silicone oil. The hydrophobic carrier preferably constitutes 50-90 wt. %, more preferably 55-85 wt. %, and most preferably 60-80 wt. % of the composition. Medium chain triglycerides (MCTs) are preferred as the hydrophobic carrier. MCTs are typically about 6 to about 12 carbons in length. MCTs can be vegetable oils. Caprylic/capric triglyceride is a non-limiting example of an MCT preferred for use in the invention.

In addition to the hydrophilic film-forming polymer and the hydrophobic carrier, the oral care compositions may optionally further contain one or more orally acceptable abrasives, flavorants, colorants, sweeteners, processing aids, and viscosity modifying agents. Viscosity modifiers are illustrated to include silicone adhesives and silicone resins.

In certain embodiments, the oral care composition comprises, consists essentially of, or consists of 1 to 10 wt. %, preferably 2.5 to 7 wt. %, and most preferably 5 wt. % high cleaning abrasive, such that the total amount of abrasive delivered per application is 2 mg to 8 mg, preferably 3 mg to 6 mg, and most preferably about 4 mg of abrasive. A small amount of small particle size abrasive provides an improved stain removal effect and occlusion effect.

It is preferred that the abrasive be selected from high cleaning silica, tetrasodium pyrophosphate (TSPP), tetrapotassium pyrophosphate (TKPP), sodium tripolyphosphate (STPP), and mixtures thereof. The abrasives typically have a weight mean particle size in the range 2 to 18 µm with at least 90% by weight of particles having a size below 20 µm, a Radioactive Dentine Abrasion (RDA) determined on an aqueous slurry of the silica powder of 90 to 230, a Pellicle Cleaning Ratio (PCR), when incorporated in a dental composition at 10 wt. %, greater than 80, the ratio of PCR to RDA being in the range 0.4:1 to less than 1:1 and having a Plastics Abrasion Value (PAV) in the range of 1 to 20.

As demonstrated in the Examples below, polyphosphates, such as TSPP and TKPP, which are conventionally defined as tartar control agents and/or abrasives, unexpectedly improve the efficacy of the anti-hypersensitivity actives in embodiments of the inventive oral care composition. Thus, certain preferred embodiments contain polyphosphates in amounts synergistically effective in combination with the film-forming polymer to treat and/or prevent dentinal hypersensitivity, e.g., wherein polyphosphates constitute 0.5-10 wt. % or 1-6 wt. % or 1-2 wt. % or 3-5 wt. % of the oral care composition, with TSPP being most preferred in amounts from 0.5 to 3 wt. % and TKPP being most preferred in amounts from 3 to 5 wt. %.

Certain embodiments comprise silicas having a particularly effective ability to clean, which is demonstrated by relatively high PCR values exhibited at conventional RDA values in oral cares containing a relatively small amount of the silica. Although the PCR to RDA ratio is less than 1, the RDA value preferably is higher than conventional silicas with a higher PCR to RDA ratio and, when compared to these products, a higher PCR is achievable with the same quantity of silica. Plastics Abrasion Values are a measure of the amount of scratching produced on a surface by the silica and are therefore indicative of possible damage to teeth. The silicas useful possess a moderate PAV but high PCR, which indicates good cleaning without excessive damage.

The silicas useful in the invention preferably have an oil absorption, using linseed oil, in the range 70 to 150 cm$^3$/100 g and, more preferably, the oil absorption is in the range 75 to 130 cm$^3$/100 g. Also, the silica preferably has a BET surface area in the range 10 to 450 m$^2$ g$^{-1}$, and, more preferably, the BET surface area is in the range 50 to 300 m$^2$ g$^{-1}$.

The weight mean particle size of the silica can be determined using a Malvern Mastersizer™ and a preferred material may have a weight mean particle size in the range 5 to 10 µm. The particle size distribution and, hence, the proportion of particles having a size below any particular value can be determined by the same technique. For the amorphous silica, at least 90% of the particles by weight preferably have a size below 17 µm.

In a particular embodiment, the weight mean particle size of the abrasives useful in the embodiments is in the range of 3 to 7 µm, with at least 90% of the particles by weight having a size below 16 µm, preferably below 12 µm.

In a particular embodiment, the silica is in the form of particles of a size such that they are effective to occlude dentinal tubules. Thus, the silica particles preferably have an average diameter of 0.5-10 microns or 1-9 microns or 2-7 microns, with an average diameter below 5 microns being most preferred.

The Radioactive Dentine Abrasion (RDA) of the silicas has a value in the range 100 to 220. More commonly, the RDA has a value in the range 120 to 200 and, frequently, the RDA is above 140. Generally, silicas having a PAV above 15 will have an RDA above 120 and those having a PAV above 17 have an RDA above 140.

The PCR (measured in a dental composition at 10% by weight) of the amorphous silica is greater than 85, preferably greater than 90 and more preferably greater than 95. The PCR:RDA ratio is preferably in the range 0.5:1 to 0.9:1.

The amorphous silica preferably has a pH value, measured on a 5% by weight suspension, in the range 5 to 8, more preferably in the range 6 to 7.5. The amount of water present on the amorphous silica suitable for use in a dental composition, as measured by the ignition loss at 1000° C., is usually up to 25% by weight and preferably up to 15% by weight. Usually the ignition loss at 1000° C. is more than 4% by weight.

Encapsulated oral care compositions and certain non-encapsulated embodiments of the inventive oral care composition comprise a hydrophobic viscosity modifier, which is as the name implies a hydrophobic ingredient, which increases the viscosity of the hydrophobic liquid. Gelled mineral oils are presently the most preferred examples of suitable hydrophobic viscosity modifiers. The gelled mineral oil is preferably a blend of mineral oil and polyethylene, and most preferably PLASTIGEL 5, which is a blend of 5% polyethylene in mineral oil, and is available from Pharmaceutical Resources/Lyne Laboratories Inc. of Brockton, Mass. Other suitable plastigels can be prepared in accordance with the teachings of Thau et al., "A New Procedure for the Preparation of Polyethylene-Mineral Oil Gels," J. Soc. Cosmetic Chemists, 16, 359-363 (1965). Suitable hydrophobic viscosity modifiers additional to gelled mineral oils, such as plastigels, can be identified by using the present disclosure as a guide.

When present, the hydrophobic viscosity modifier preferably constitutes 1-50 wt. % or 3-5 wt. % or 30-40 wt. % of the oral care composition.

Colorants such as pigments and dyes may be used in the composition. Pigments include nontoxic, water insoluble inorganic pigments such as titanium dioxide and chromium oxide greens, ultramarine blues and pinks and ferric oxides. The pigments have a particle size in the range of 5-1000 microns, preferably 250-500 microns, and are present at a concentration of 0.5 to 3% by weight.

Dyes used are generally food color additives presently certified under the Food Drug & Cosmetic Act for use in the food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of ethyl-[4-[[4-[ethyl-[(3-sulfophenyl)methyl]amino]phenyl]-(4-hydroxy-2-sulfophenyl)methylidene]-1-cyclohexa-2,5-dienylidene]-

[(3-sulfophenyl)methyl]azanium), FD&C Blue No. 1 (disodium salt of dibenzyldiethyldiaminotriphenyl-carbinol trisulfonic acid of indigotin) and mixtures thereof in various proportions. Preferred dye concentrations range from 0.0005 to 1% of the total weight.

Any suitable flavoring or sweetening agent may also be incorporated in the oral care composition. Examples of suitable flavoring constituents include flavoring oils, as for example, oils of spearmint, peppermint, wintergreen, sassafras, clove, sage, eucalyptus, marjoram, cinnamon lemon, and orange, and methyl salicylate. Suitable sweetening agents include sucrose, sucralose, lactose, maltose, sorbitol, xylitol, sodium cyclamate, perillatine, and sodium saccharin. Suitably, flavoring materials are included in the oral care composition in an amount of 5% to 25% by weight, more preferably 10% to 20% by weight, and most preferably about 15% by weight. The sweetening agents may comprise 0.1 to 5% by weight, more preferably 0.25 to 2% by weight, and most preferably about 0.5% by weight of the oral care components.

Oral care compositions of the invention are non-aqueous and thus contain relatively low amounts of water. In certain embodiments, the compositions comprise less than 10 wt. % or less than 5 wt. % or less than 1 wt. % water. The total amount of water in the oral care compositions includes contributions from water intentionally added as a component and water present as contaminant, constituent, byproduct or solvent for various other components. In preferred embodiments, the oral care compositions are formulated without adding water as a separate component. The resulting water content of the oral care composition is then derived from the water present as a contaminant, constituent, byproduct or solvent for the various components.

The oral compositions optionally contain one or more other non-active ingredients. Non-limiting examples include diluents, bicarbonate salts, pH modifying agents, foam modulators, thickening agents, viscosity modifiers, pigmenting agents, sweetening agents, flavorants and colorants. Tooth pastes, tooth gels, and other oral care compositions are formulated with these and optionally other additives according to known principles.

Certain embodiments of the oral care composition are encapsulated in a gelatin capsule. Encapsulating liquid or aqueous compositions in a gelatin capsule can be accomplished using techniques known in the art and described in, for example, U.S. Pat. Nos. 4,422,985, 4,426,337 and 5,478,570. The process typically entails forming a jet of the oral care composition and a jet of the coating material (e.g., gelatin) coaxial with the jet of oral care composition, heating the coaxial jets (optionally with a third coaxial heating element or hot air) and introducing the components into a cooling liquid to form capsules formed of the oral care composition, coated with the gelatin. Although the oral care composition is preferably prepared in the absence of alcohol, any alcohol present in the oral care preferably is evaporated during the heating of the respective components. Preferably, the gelatin comprises from 6 to 15% of the total weight of the encapsulated oral care composition (i.e., the capsule and the oral care composition), more preferably 8 to 12%, and most preferably about 9%. Similarly, the oral care composition comprises 85 to 94% of the total weight of the encapsulated oral care composition, more preferably 88 to 92, and most preferably about 91%.

The composition has been described above with respect to several preferred embodiments. Further non-limiting description is provided in the Examples that follow.

EXAMPLES

Example 1

An anti-sensitivity wax for deliver from stick applicator was prepared from the following ingredients.

TABLE 1

| Ingredient | Parts by Weight |
| --- | --- |
| Beeswax | 20 |
| Shea Butter | 20 |
| Palm Kernel Oil | 15 |
| Castor Oil | 37.5 |
| L-Arginine | 5 |
| GANTREZ S-97 (BF) | 2 |
| Flavor | 0.4 |
| Sweetener | 0.1 |
| TOTAL | 100 |

Example 2

An anti-sensitivity composition in the form of a paint-on gel was prepared from the following ingredients.

TABLE 2

| Ingredient | Parts by Weight |
| --- | --- |
| Silicon Adhesive | 29 |
| Silicon Fluid | 27 |
| Gantrez S-97 | 2.5 |
| Plastigel 5 | 35 |
| Potassium Nitrate | 5 |
| Flavor | 1.2 |
| Sweetener | 0.3 |
| TOTAL | 100 |

Examples 3-11

Compositions were tested for dentinal fluid flow using hydraulic reduction methods. Dentinal fluid flow was measured with a flow-meter (Flodec) attached to dentin segments. The oral care compositions were applied using a finger tip onto the dentin mounted on an acrylic block for one minute. Excess oral care composition was rinsed from the disks with PBS and the flow was recorded under simulated pulpal pressure of 70 cm $H_2O$.

Each sample disk was tested before and after oral care application in order to provide its own baseline. After treatment, samples with flow reduction of 40% and higher are considered for the anti-hypersensitivity benefit via dentinal occlusion.

TABLE 3

| Example | 3 | 4 | 5 | 6 | 7 |
| --- | --- | --- | --- | --- | --- |
| Formulas | HighPCC/Arg | 2% Gantrez acid | 5% Gantrez acid | Ca. Gantrez | 2% Gan. acid + 5% Arg |
| % Flow Reduction | 40.65 | 69.13 | 74.99 | 54.38 | 61.56 |
| Standard Deviation | 4.57 | 11.51 | 2.12 | 8.93 | 21.61 |
| Ingredients | | | | | |
| Caprylic/capric triglyceride | 66.5 | 76.5 | 73.5 | 76.5 | 71.5 |
| L-Arginine | 5.0 | 0.0 | 0.0 | 0.0 | 5.0 |

TABLE 3-continued

| Example | 3 | 4 | 5 | 6 | 7 |
|---|---|---|---|---|---|
| Gantrez S-97 (B.F) | 0.0 | 2.0 | 5.0 | 0.0 | 2.0 |
| Gantrez MS-955 (Ca Gantrez) | 0.0 | 0.0 | 0.0 | 2.0 | 0.0 |
| TKPP Fine Powder | 0.0 | 0.0 | 0.0 | 0.0 | 0.0 |
| TSPP | 0.0 | 0.0 | 0.0 | 0.0 | 0.0 |
| Plastigel | 0.0 | 0.0 | 0.0 | 0.0 | 0.0 |
| Flavor | 15.0 | 15.0 | 15.0 | 15.0 | 15.0 |
| WS3 cooling | 1.5 | 1.5 | 1.5 | 1.5 | 1.5 |
| Sucralose | 0.5 | 0.5 | 0.5 | 0.5 | 0.5 |
| EtOH | 4.5 | 4.5 | 4.5 | 4.5 | 4.5 |
| Citric Acid | 2.0 | 0.0 | 0.0 | 0.0 | 0.0 |
| High Absorption PCC | 5.0 | 0.0 | 0.0 | 0.0 | 0.0 |
| Total | 100.0 | 100.0 | 100.0 | 100.0 | 100.0 |

TABLE 4

| Example | 8 | 9 | 10 | 11 |
|---|---|---|---|---|
| Formulas | 1.2% Gan. acid + 3.2% Arg | 1.2% Gan. acid + 3.2% Arg + 1.35% TSPP | 1.2% Gan. acid + 3.2% Arg + 4% TKPP | 1.2% Gan. acid + 3.2% Arg + 4% TKPP + 1.35% TSPP |
| % Flow Reduction | 7.40 | 42.07 | 56.50 | 84.58 |
| Standard Deviation | 0.22 | 2.66 | 9.90 | 1.42 |
| Ingredients | | | | |
| Caprylic/capric triglyceride | 67.1 | 65.75 | 66.1 | 64.75 |
| L-Arginine | 3.2 | 3.2 | 3.2 | 3.2 |
| Gantrez S -97 (B.F) | 1.2 | 1.2 | 1.2 | 1.2 |
| Gantrez MS-955 (Ca Gantrez) | 0 | 0 | 0 | 0 |
| TKPP Fine Powder | 0 | 0 | 4 | 4 |
| TSPP | 0 | 1.35 | 0 | 1.35 |
| Plastigel | 0 | 0 | 4 | 4 |
| Flavor | 15 | 15 | 15 | 15 |
| WS3 cooling | 1.5 | 1.5 | 1.5 | 1.5 |
| Sucralose | 0.5 | 0.5 | 0.5 | 0.5 |
| EtOH | 4.5 | 4.5 | 4.5 | 4.5 |
| Citric Acid | 2 | 2 | 0 | 0 |
| High Absorption PCC | 5 | 5 | 0 | 0 |
| Total | 100 | 100 | 100 | 100 |

The foregoing Examples show that non-aqueous oral care compositions of the invention will be effective to treat and/or prevent dentinal hypersensitivity. The data in Table 4 show that polyphosphates surprisingly improve the efficacy of the anti-hypersensitivity actives. In particular, the addition of 1.35 wt. % TSPP to the composition of Example 8 increased the percent reduction from 7.4% to 42.07% (see Example 9) the addition of 4 wt. % TKPP to the composition of Example 8 increased the percent reduction from 7.4% to 56.5% (see Example 10), and the addition of 1.35 wt. % TSPP and 4 wt. % TKPP to the composition of Example 8 increased the percent reduction from 7.4% to 84.58% (see Example 11).

The invention has been described above with respect to various preferred aspects; however it is to be understood the invention is not limited to the disclosed embodiments. Variations and modifications that will occur to the person of skill in the art are also part of the invention, which is defined in the appended claims.

What is claimed is:

1. A oral care composition comprising:
   (a) a hydrophilic film-forming polymer; and
   (b) a hydrophobic carrier,
   wherein the polymer is effective to occlude dentinal tubules and the oral care composition contains less than 10 wt. % water,
   wherein the hydrophilic film-forming polymer constitutes 2-5 wt. % of the oral care composition and is an acid form of a copolymer of maleic anhydride,
   wherein the hydrophobic carrier constitutes 55-85 wt % of the oral compositions, and wherein the oral care composition further comprises a polyphosphate
   wherein the polyphosphate constitutes 1-7 wt. % of the oral care composition and comprises at least one member selected from the group consisting of TetraPotassium Pyrophosphate (TKPP) and Tetra Sodium Pyrophosphate (TSPP), and combinations thereof; and
   wherein the oral composition comprises arginine.

2. The oral care composition of claim 1, wherein the oral care composition contains less than 1 wt. % water.

3. The oral care composition of claim 1, wherein the hydrophobic carrier comprises at least one member selected from the group consisting of an oil, a wax and silicone.

4. The oral care composition of claim 3, wherein the hydrophobic carrier comprises vegetable oil and/or silicone oil.

5. The oral care composition of claim 4, wherein the hydrophobic carrier comprises a C6 to C12 triglyceride.

6. The oral care composition of claim 1, wherein the polyphosphate constitutes 1-7 wt. % of the oral care composition.

7. The oral care composition of claim 1, having a flow reduction greater than 60% as measured with a flow-meter attached to a Pashley's cell.

8. The oral care composition of claim 1, wherein the oral care composition further comprises 5-25 wt. % of a flavoring agent and 0.1-5 wt. % of a sweetening agent.

9. The oral care composition of claim 1, wherein the oral care composition further comprises at least one member selected from the group consisting of an abrasive, an antibacterial agent, a foaming agent, a whitening agent, an anti-calculus agent, a tartar control agent, an anti-inflammatory agent, an anticaries agent, a flavoring agent, a sweetening agent and a colorant.

10. The oral care composition of claim 1, wherein the oral care composition is encapsulated within a capsule comprising gelatin.

11. The oral care composition of claim 1, wherein the oral care composition is a solid at 21° C.

12. A method of cleaning teeth comprising applying to the teeth the oral care composition of claim 1 such that the hydrophilic film-forming polymer occludes dentinal tubules.

13. A toothbrush comprising:
   a handle;
   a head mounted to the handle, the head comprising an outer surface and a plurality of tooth cleaning elements extending outwardly from the outer surface; and
   a gelatin capsule containing the oral care composition of claim 1 positioned on the head.

* * * * *